(12) United States Patent
De Groote

(10) Patent No.: US 8,586,629 B2
(45) Date of Patent: Nov. 19, 2013

(54) COMPOSITION FOR THE TREATMENT OF OXIDATIVE STRESS

(75) Inventor: Donat Eugene H. De Groote, Waterloo (BE)

(73) Assignee: Probiox SA, Liege (BE)

( * ) Notice: Subject to any disclaimer, the term of this patent is extended or adjusted under 35 U.S.C. 154(b) by 365 days.

(21) Appl. No.: 12/851,900

(22) Filed: Aug. 6, 2010

(65) Prior Publication Data

US 2012/0009276 A1 Jan. 12, 2012

Related U.S. Application Data

(63) Continuation-in-part of application No. PCT/EP2009/000836, filed on Feb. 6, 2009.

(30) Foreign Application Priority Data

Feb. 8, 2008 (GB) .................................. 0802403.6

(51) Int. Cl.
*A61K 45/06* (2006.01)
*A61K 33/32* (2006.01)
*A61K 31/315* (2006.01)

(52) U.S. Cl.
USPC ............................ 514/494; 424/641; 424/639

(58) Field of Classification Search
USPC .................................. 424/639, 641; 514/494
See application file for complete search history.

(56) References Cited

U.S. PATENT DOCUMENTS

| | | | |
|---|---|---|---|
| 5,935,996 A | 8/1999 | Yamaguchi | |
| 2003/0108624 A1 | 6/2003 | Kosbab | |
| 2003/0194453 A1* | 10/2003 | Coleman et al. | 424/736 |
| 2006/0057186 A1* | 3/2006 | Heller | 424/439 |
| 2008/0003303 A1 | 1/2008 | Chien et al. | |
| 2008/0031940 A1 | 2/2008 | Rodriguez | |

OTHER PUBLICATIONS

Andriollo-Sanchez, et al., "No Antioxidant Beneficial Effect of Zinc Supplementation on Oxidative Stress Markers and Antioxidant Defenses in Middle-Aged and Ederly Subjects: The Zenith Study", Journal of the American College of Nutrition, vol. 27, No. 4, pp. 463-469, 2008.
Bao et al., Zinc supplementation decreases oxidative stress, incidence of infection, and generation of inflammatory cytokines in sickle cell disease patients, Translational Research, vol. 152, No. 2, 2008.
Berg et al., "Effect of oral contraceptive progestins on serum cooper concentration", European Journal of Clinical Nutrition 52, pp. 711-715, 1998.
Bhat et al., "Critical role of oxidative stress in estrogen-induced carcinogenesis", PNAS, vol. 100, No. 7, pp. 3913-3918, Apr. 1, 2003.
Chamblis et al., "Estrogen Modulation of Endothelial Nitric Oxide Synthase", The Endocrine Society, Endocrine Reviews, 23(5), pp. 665-686, 2002.

(Continued)

Primary Examiner — Rachael E Bredefeld
(74) Attorney, Agent, or Firm — Dinsmore & Shohl LLP

(57) ABSTRACT

This invention is based on the observed oxidative stress and increased risk on cardiovascular diseases in subjects with increased lipid peroxidation, in particular with women using oral contraceptives and in hormone replacement therapies. The invention provides compositions and combinations, particularly useful in preventing and or reducing the increased lipid peroxidation in subjects in need thereof. These compositions are based on the synergistic combination of zinc and/or a hydroxyl radical scavenger in reducing lipid peroxidation.

12 Claims, 11 Drawing Sheets

(56) References Cited

OTHER PUBLICATIONS

Edwards et al., "Quercetin Reduces Blood Pressure in Hypertensive Subjects 1,2", The Journal of Nutrition, Nutrition and Disease, pp. 2405-2411, 2007.
Fellet-Coudray et al., "Effect of zink supplementation on in vitro copper-induced oxidation of low-density lipoproteins in healthy French subjects aged 55-70 years: the Zenith Study", British Journal of Nutrition 95, pp. 1134-1142, 2006.
Ferns et al., "The posible rol of copper ions in atherogenesis: the Blue Janus", Atherosclerosis 133, pp. 139-152, 1997.
Gaetke et al., "Copper toxicity, oxidative stress, and antioxidant nutrients", Toxicology 189, pp. 146-163, 2003.
Gordon et al., "Effects of 17h-oestradiol on cerebral ischaemic damage and lipid peroxidation", Brain Research 1036, pp. 155-162, 2005.
Itagaki et al., "Opposing effectsof oestradiol and progesterone on intracellular pathways and activation processes in the oxidative stress induced activation of cultured rat hepatic stellate cells", gut.bmj-journals.com, pp. 1782-1799, 2005.
Kirkil et al., "Antioxidant effect of zinc picolinate in patients with chronic obstructive pulmonary disease", Respiratory medicine 102, pp. 840-844, 2008.
Laufs et al., "Down-regulation of Rac-1 GTPase by Estrogen", The Journal of Biological Chemistry, Vo. 278, No. 8, Issue of Feb. 21, pp. 5956-5962, 2003.
Patel et al., "Reduction of Cu(II) by lipid hydroperoxides: implications for the copper-dependent oxidation of low-density lipoprotein", Biochem J. 332, pp. 425-433, 1997.
Saul R. Powell, "The Antioxidant Properties of Zinc 1,2", The Journal of Nutrition, American Society for Nutritional Sciences, Zinc and Heath: Current Status and Future Directions, 2000.
Prasad et al, "Antioxidant Effect of Zinc in Humans", Free Radical Biology & Medicine, vol. 37, No. 8, pp. 1182-1190, 2004.
Prasad et al., "Zinc supplementation decreases incidence of infections in the elderly: effect of zinc on generation of cytokines and oxidative stress 1-3" The American Journal of Clinical Nutrition 85, pp. 837-844, 2007.
Prokai-Tatrai et al., "Impact of Metabolism on the Safety of Estrogen Therapy", New York Academy of Sciences 1052, pp. 243-257, 2005.
Roussel et al., "Antioxidant Effects of Zinc Supplementation in Tunisians with Type 2 Diabetes Mellitus", Journal of the American College of Nutrition, vol. 22, No. 4, pp. 316-321 (2003).
Strehlow et al., "Modulation of Antioxidant Enzyme Expression and Function by Estrogen", Estrogen and SOD, Circulation Research pp. 172-177, Jul. 25, 2003.
Uriu-Adams et al, "Copper, oxidative stress, and human health", Molecular Aspects of Medicine 26, pp. 268-298, 2005.
Wagner et al, "17B-Estradiol inhibition of NADPH oxidase expression in human endothelial cells", The FASEB Journal, vol. 15, pp. 2121-2130, Oct. 2001.
Wassmann et al., "Progesterone Antagonizews the Vasoprotective Effect of Estrogen on Antioxidant Enzyme Expression and Function", Progesterone and SOD, pp. 1046-1054, Circulation Research Nov. 11, 2005.
Terao et al, "Anti-atherosclerotic effect of dietary flavonoids: Quercetin glucoside attenuates lipid peroxidation in rabbit aorta", Free Radical Biology & Medicine, vol. 36, No. Suppl. 1, 2004, p. S33.
Baltaci et al, "The effects of zinc deficiency and supplementation on lipid peroxidation in bone tissue of ovariectomized rats", Toxicology, Limerick, IR, vol. 203, No. 1-3, Oct. 15, 2004.
Ozturk et al., "Effects of Zink Deficiency and Supplementation on Malondialdehyde and Glutathione Levels in Blood and Tissues of Rats Performing Swimming Exercise", Biological Trace Element Research, vol. 94, No. 2, Aug. 2003.
Yao et al., "Quercetin protects human hepatocytes from ethanol-derived oxidative stress by inducing heme oxygenase-1 via the MAPK/Nrf2 pathways", Journal of Hepatology, Munksgaard International Publishers, Copenhagen, DK, vol. 47, No. 2, Jul. 10, 2007.
Pincemail et al., "Effect of different contraceptive methods on the oxidative stress status in women aged 40-48 years from ELAN study in the province of Liège, Belgium", Human Reproduction (Oxford), vol. 22, No. 8, Aug. 2007, pp. 2335-2343.
Farinati et al, "Zinc treatment prevents lipid peroxidation and increases glutathione availability in Wilson's disease", Journal of Laboratory and Clinical Medicine, vol. 141, No. 6, Jun. 2003, pp. 372-377.
PCT/EP2009/000836 International Search Report and Written Opinion dated Aug. 27, 2009.

* cited by examiner

COMPOSITION FOR THE TREATMENT OF OXIDATIVE STRESS

CROSS REFERENCE TO RELATED APPLICATIONS

This application is filed under 35 U.S.C. 111(a) as a continuation-in-part of International Patent Application No. PCT/EP2009/000836, filed Feb. 6, 2009, which application designates the United States and claims the benefit of United Kingdom Application No. 0802403.6 filed Feb. 8, 2008.

FIELD OF THE INVENTION

This invention is based on the observed oxidative stress and increased risk on cardiovascular diseases in subjects with increased lipid peroxidation, in particular with women using oral contraceptives and in hormone replacement therapies.

The invention provides compositions and combinations, particularly useful in preventing and/or reducing the increased lipid peroxidation in subjects in need thereof. These compositions are based on the synergistic combination of zinc and/or a hydroxyl radical scavenger, with other agents used in oral contraceptive or hormone replacement therapy. In particular the combination of zinc and quercetin, optionally in combination with other agents used in ROS induced pathologies, more in particular in the treatment or prevention of ROS induced pathologies in women on oral contraceptive treatment or hormone replacement therapy.

BACKGROUND TO THE INVENTION

Oxidative stress is defined as an imbalance between antioxidant and reactive oxygen species (ROS) in favour of the latter. ROS, which include free radicals, are continuously produced in the body and play an important physiological role at low concentrations. They act as second messengers capable of modulating the expression of various genes involved in immune response. Various conditions, e.g. sun exposure, intense exercise, smoking habits, chronic inflammation, metal poisoning, mitochondrial dysfunction, or hyperglycaemia can, however, lead to a non-physiological production of ROS and will cause irreversible cell lesions that are linked to the development of several human pathologies including, atherosclerosis, cardiovascular disease, cancer, diabetes complications, muscular degeneration and arthritis.

Since the discovery that oral progestational 19-nor steroids could inhibit ovulation (Chang et al, *Science* 1956 124; 890-891), several million woman have used different types of synthetic estrogens and progestins to prevent conception. In post-menopausal women, hormone replacement therapy (HRT) is based on the intake of different types of hormones involving estrogens (namely estradiol and conjugated estrogens) and natural progesterone or synthetic progestins in order to replace the failing ovarian secretion.

Apart from their gynaecologic influence, the hormones have been shown to affect a number of metabolic and nutritional processes, some advantageously and others disadvantageously. Their relationship with oxidative stress has been a matter of ongoing discussion. Estrogens are recognized to be beneficial in the prevention of atherosclerosis although they are capable of inducing oxidative stress, which is involved in the development of the same atherosclerosis. A recent study (Pincemail et al., *Human Reproduction* 2007; 2335-2343), indicates that the intake of estrogens is associated with a significantly altered Oxidative Stress among women aged 40-48 years.

The objective of the present invention is to provide a therapy to reduce the oxidative stress induced pathologies, hereinafter also referred to as ROS induced pathologies, which for example results in a increased lipid peroxidation, in subjects in need thereof; in particular to reduce ROS induced pathologies in women using oral contraceptives and in hormone replacement therapy. An improvement of oxidative stress status in said subjects can be assessed using the parameters mentioned in the clinical study hereinafter and typically include a significant reduction of the lipidic peroxides, oxidized LDL or both parameters in said subjects, preferably with a normalization of the Cu/Zn ratio.

Clinical studies as to the antioxidant effect of zinc in a variety of disease states and patient populations demonstrate that there is no uniform response throughout the different disease states and patient populations with sometimes even contradictory effects. A study to the effect of zinc supplementation on the occurrence of infections of healthy elderly people (Am. J. Clin. Nutr. 2007, 85 (3):837-44) found that the incidence of infection was significantly lower in the zinc supplemented group with a reduction in oxidative stress markers including a significant diminution of lipid peroxides. This in contrast to a more recent study as to the beneficial effects of zinc supplementation on oxidative stress markers and antioxidant defences in middle-aged and elderly people (J. Am. Coll. Nutr. 2008, 27 (4):463-9). Contrary to the previous study, zinc supplementation did not alter oxidative stress markers and had no effect on the oxidative stress status of said individuals. Similar results were found in a study to the effects of zinc supplementation on in vitro copper-induced oxidation of LDL in healthy French subjects aged 55-70 years (Br. J. Nutr., 2006, 95 (6):1134-42). Again no effects of zinc supplementation on Cu-induced LDL oxidation were found.

Even in study populations known to experience oxidative stress, such as for example in patients with chronic obstructive pulmonary disease, hypobaric hypoxia, type 2 diabetes mellitus (T2DM) and sickle cell disease patients; there is no uniform effect of zinc supplementation on oxidative stress markers and in particular on lipid peroxidation products. In the hypobaric hypoxia studies (Aviat. Space Environ. Med. 2004, 75 (10):881-8; Wilderness Eniron. Med. 1999, 10 (2):66-74) and the COPD study (Respir. Med. 2008, 102 (6):840-4) no effects were found for zinc supplementation on the oxidative stress markers in said subjects. This in contrast to the studies in T2DM (J. Am. Coll. Nutr. 2003, 22 (4):316-21) and sickle cell disease (Transl. Res. 2008, 152 (2):67-80) which suggest that zinc supplementation may be beneficial in said patients.

Despite the generally accepted fact that hydroxyl radical scavengers like flavonoids, and in particular quercetin, are potent antioxidants in vitro, with quercetin being the most effective inhibitor of oxidative damage to LDL in vitro, numerous studies indicate that this effect is absent in vivo. See for example the study on the effects of a high flavonoid diet in healthy volunteers (Free Radic. Res. 2000, 33 (4):419-426) where no significant difference was found in the $Cu^{2+}$ ion-stimulated lag-time of LDL oxidation between the high and low flavonoid dietary treatments. In another study in normocholesterolaemic female volunteers (Eur. J. Clin. Nutr. 2000, 54 (10):774-82), a 6 week rutin supplementation significantly elevated the levels of three plasma flavonoids but had no effect on plasma antioxidant status. Even in study populations with oxidative damage/stress, such as for example in athletes with exercise-induced damage and inflammation (Appl. Physiol. Nutr. Metab. 2008, 33 (2):254-62) or in hypertensive subjects, including both men and women (J. Nutr. 2007, 137 (11):2405-2411), quercetin supplementation does not exert protection from oxidative stress induced damage, and does not result in a reduction of systemic markers of oxidative stress in said studies. This different behaviour of hydroxyl radical scavengers like flavonoids, and in particular quercetin, in an in vivo environment vis-à-vis an ex vivo (in vitro) environment was also found in a study to investigate whether in vivo supplementation with red wine extracts and quercetin can have an effect on the oxidative resistance of LDL (Clin. Chem. 2000, 46 (8 Pt1):1162-70). In this study no effects were found for the parameters directly assessed in the plasma of said patients, but only for an ex vivo determination of the LDL oxidizability.

SUMMARY OF THE INVENTION

This invention is based on the observation that zinc supplementation; supplementation with a hydroxyl radical scavenger; or the combination of a hydroxyl radical scavenger and zinc is particularly useful in preventing and or reducing the increased lipid peroxidation in subjects, in particular with women using oral contraceptives and in hormone replacement therapies.

It is accordingly an objective of the present invention to provide a combination of first component (a) which is zinc and a second component (b) which is a hydroxyl radical scavenger for use in a method of reducing lipid peroxidation in a subject in need thereof.

In another objective, the present invention provides zinc, either alone or in combination with a hydroxyl scavenger for use in preventing and or reducing the increased lipid peroxidation in subjects, in particular with women using oral contraceptives and in hormone replacement therapies. It accordingly provides the use of zinc, either alone or in combination with a hydroxyl scavenger, in the manufacture of a medicament for preventing and or reducing the increased lipid peroxidation in subjects, in particular in women using oral contraceptives and in hormone replacement therapies.

Alternatively, the present invention provides a hydroxyl scavenger, either alone or in combination with zinc for use in preventing and or reducing the increased lipid peroxidation in subjects, in particular with women using oral contraceptives and in hormone replacement therapies. It accordingly provides the use of a hydroxyl scavenger, either alone or in combination with zinc, in the manufacture of a medicament for preventing and or reducing the increased lipid peroxidation in subjects, in particular in women using oral contraceptives and in hormone replacement therapies.

As used in the different embodiments of the present invention, the hydroxyl radical scavenger is selected from the group consisting of phytonutriments, e.g. green tea, centaurium erythrea, allium savitum; polyphenolic compounds, e.g. rutin, quercetin, genistein; Maltol; Nordihydroguaiaretic Acid (NDGA); Thymoquinone; Galloyl quinic derivatives; Indole-3-proprioate; N-acetyl cysteine; Ergothioneine; Citrullin; 5-Hydroxytryptophan (5-HTP); Alliin; Melatonin; Mannitol; Erythritol; Sialic acid; Deoxyribose; Lazaroids (21-aminosteroids) e.g. U74389G, U78517F, U74389F, U74500A; GSH analogs e.g. UPF1; Vitamin-C derivatives, e.g. EPC-K1; Fullerene derivatives (carbon nanotubes), e.g. Cystine c(60) derivative (CFD), Beta-alanine c(60) derivative, Alpha-alanine c(60) derivative and Others, e.g. Edaravone (MCI-186), Amlodipine, Rebamipide, Carbocysteine lysine salt monohydrate (SCMC-Lys), Ursodiol (ursodeoxycholic acid—UDCA-), Iron choline E6 (FeCe6), Betaine, Trimidox (VF233), (±)-N,N'-propylenedinicotinamide (AVS). In a particular embodiment the hydroxyl scavenger is a polyphenolic compound; more in particular a polyphenolic compound selected from the group consisting of rutin, quercetin, genistein, resveratrol, oleuropein, pycnogenol, procyanidin C1, and daidzein.

In an even further embodiment of the present invention the hydroxyl radical scavenger is selected from the group consisting of quercetin, genistein, resveratrol, oleuropein, pycnogenol, procyanidin C1, daidzein, thymoquinone, N-acethyl cysteine, Citrullin, and 5-Hydroxytryptophan (5-HTP); more in particular the hydroxyl radical scavenger as used in the different embodiments of the present invention consists of quercetin.

In the different embodiments of the present invention, zinc is selected from the group consisting of mineral zinc, mineral zinc complexes or zinc salts, e.g. zinc oxide; zinc pyrithione; zinc acetate; zinc gluconate; zinc picolinate; zinc sulfate; zinc citrate; zinc glycerate; zinc monomethionine; zinc aspartate; zinc lactate, zinc malate; zinc tartrate; orotate and zinc aninoacid chelates.

In a particular embodiment, the present invention provides a combination consisting essentially of mineral zinc and a polyphenolic compound (in particular quercetin); and wherein said combination is provided as a food supplement or a pharmaceutical compositions. It is also an object of the present invention, and as provided in more detail hereinafter, to provide the aforementioned components and combinations in a pharmaceutical composition further comprising one or more agents typically used in oral contraception or in hormone replacement therapy.

In a second objective, the present invention provides a kit of parts comprising;
 a first component which is an amount of zinc in a first unit dosage form; and
 a second component which is an amount of a hydroxyl radical scavenger in a second unit dosage form.

The first and second component in the aforementioned applications, combinations and kit of parts, are suitable for sequential, separate and/or simultaneous use in treating oxidative stress disorders. In a third objective the present invention provides the use of the aforementioned components; combinations; a kit of parts; or pharmaceutical composition(s), in the manufacture of a medicament to reduce lipid peroxidation in a subject in need thereof.

A subject in need of a reduction in lipid peroxidation, includes and in particular consist of, people using oral contraceptives and estrogens, such as women on oral contraceptive treatment and hormone replacement therapy. An increased lipid peroxidation is linked to the development of several human ROS induced pathologies including, atherosclerosis, cardiovascular disease, cancer, diabetes complications, muscular degeneration and arthritis.

It is accordingly a fourth objective of the present invention, to provide a method of treating ROS induced pathologies selected from the group consisting of atherosclerosis, cardiovascular disease, cancer, diabetes complications, muscular degeneration and arthritis in a mammal, said method comprising administering a hydroxyl scavenger, either alone or in combination with zinc; zinc either alone or in combination with a hydroxyl scavenger; any of the combinations according to the invention; or a pharmaceutical composition according to the invention, to said mammal in need thereof. In one embodiment, the present invention provides a method of treating ROS-induced atherosclerosis or ROS induced cardiovascular disease in a mammal, said method comprising administering to said mammal the components as defined hereinbefore, a combination according to the invention; or a pharmaceutical composition according to the invention. In a particular embodiment, the present invention provides a method of treating ROS induced atherosclerosis and/or cardiovascular disease in a women on oral contraceptive treatment or hormone replacement therapy, said method comprising administering to said woman a combination; or a pharmaceutical composition according to the invention.

In any of the foregoing the zinc and hydroxyl radical scavenger are administered in the same or separate pharmaceutical compositions; and may be administered sequentially, separately and/or simultaneously.

DESCRIPTION OF THE INVENTION

Figure 1:
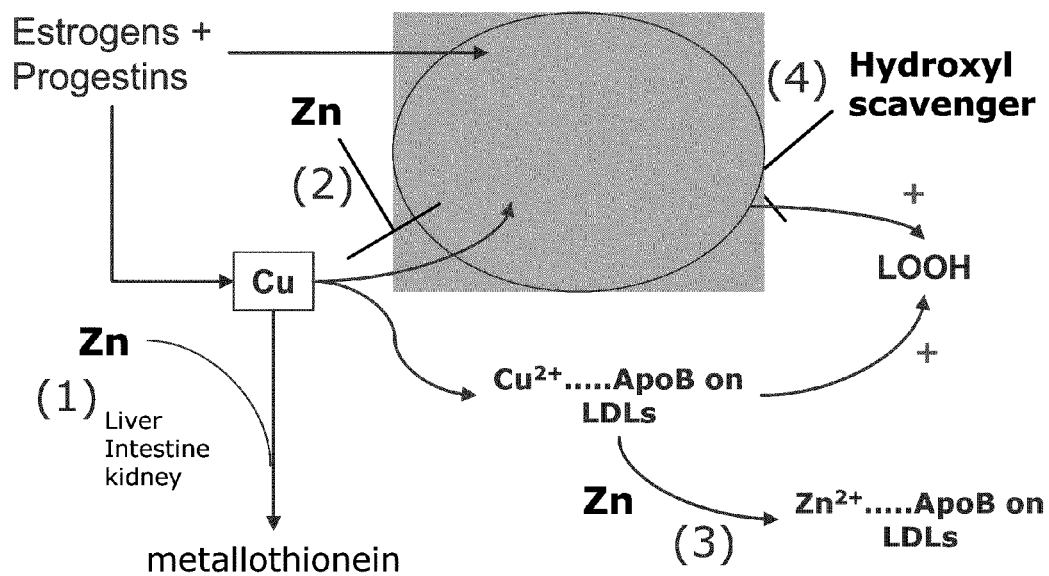
FIG. 1: use of a combination of zinc and of a hydroxyl radical scavenger to block the OC-induced oxidative stress process Zinc (1) stimulates the formation of metallothionein, which prevent Cu adsorption/uptake in the intestine, liver and kidney, (2) antagonizes copper catalyze of hydroxyl production from superoxide and $H_2O_2$ and (3) remove copper from binding site where it cause radicals formation. (4) Remaining hydroxyl radicals will then be eliminated by a specific scavenger.

As already mentioned hereinbefore, the present invention is based on the finding that a treatment of lipid peroxidation, in particular lipid peroxidation in women on oral contraceptive treatment or hormone replacement therapy, with zinc and/or a hydroxyl radical scavenger (in particular a phenolic compound) has previously unrecognized benefits for the subject in need thereof. As for example provided in more detail in the examples hereinafter, in one aspect of the present invention the treatment of lipid peroxidation, in particular lipid peroxidation in women on oral contraceptive treatment or hormone replacement therapy, consists of the combination of zinc with a hydroxyl radical scavenger. This combination, and in particular the combination of mineral zinc with a polyphenolic compound (e.g. rutin, quercetin, genistein, resveratrol, oleuropein, pycnogenol, procyanidin C1, and daidzein) has previously unrecognized benefits for the subject in need thereof.

When combinations of the therapeutic agents described herein, e.g. zinc and a polyphenolic compound as hydroxyl radical scavenger (e.g. rutin, quercetin, genistein, resveratrol, oleuropein, pycnogenol, procyanidin C1, and daidzein) are employed, unexpected synergistic effects are observed. The combinations of the present invention, and in particular the combination of zinc and quercetin, results in a more effective prevention or preferably treatment of the oxidative stress induced lipid peroxidation and the ROS induced pathologies specified herein.

If taken simultaneously, this results not only in a further enhanced beneficial, especially a synergistic, therapeutic effect, but also in additional benefits resulting from the simultaneous treatment such as a surprising prolongation of efficacy, a broader variety of therapeutic treatment and surprising beneficial effects to ROS induced pathologies in particular selected from atherosclerosis and cardiovascular disorders in women on oral contraceptive treatment or hormone replacement therapy.

Moreover, for a human patient, especially for elderly people, it is more convenient and easier to remember to take two tablets at the same time, e.g. before a meal, than staggered in time, i.e. according to a more complicated treatment schedule. More preferably, both active ingredients are administered as a fixed combination, i.e. as a single tablet, in all cases described herein. Taking a single tablet is even easier to handle than taking two tablets at the same time. Furthermore, the packaging can be accomplished with less effort.

But even when taken in isolation, each of the components of the aforementioned combinations has a beneficial effect in the treatment or prevention of ROS induced pathologies, more in particular in the treatment or prevention of ROS induced pathologies in women on oral contraceptive treatment or hormone replacement therapy Reactive oxygen species (ROS) induced pathologies treated by the methods and pharmaceutical compositions described herein include atherosclerosis, cardiovascular disease, cancer, diabetes complications, muscular degeneration and arthritis. In particular embodiments the ROS induced pathologies include atherosclerosis and cardiovascular disease.

In an even further embodiment the methods and pharmaceutical compositions of the present invention are used to treat ROS induced atherosclerosis and/or cardiovascular disorders in women on oral contraceptive treatment or hormone replacement therapy (HRT).

By "cardiovascular disorder" is meant the class of diseases that involve the heart and/or blood vessel (arteries and veins), including coronary artery disease, dysrhythmias, cardiomyopathy, and vascular disease.

"Oral Contraceptive treatment" as used herein comprises administering an estrogen and/or a progestin and/or a cyproterone to a subject in need thereof. The estrogens include for example ethinyl estradiol and mestranol. The progestrins include for example drospirenone, gestoden, levonogestrel, norethylnodrel, norchindrone, norethindrone acetate, norgestimate, desogestrel, ethynodiol diacetate, and norgestrel. The cyproterone includes for example cyproterone acetate an antiandrogen that is used in some combined oral contraceptive pills.

As indicated above, the zinc as used herein includes mineral zinc; mineral zinc complexes or zinc salts.

As used in the different combinations, kits of parts and pharmaceutical compositions of the present invention, the hydroxyl radical scavengers can be highly purified natural compounds or their synthetic counterparts.

One skilled in the art will recognize that the daily hydroxyl radical scavenger dosages required in practicing the invention, i.e. the therapeutically effective amount of hydroxyl radical scavengers of the present invention is the amount sufficient to reduce the ROS induced pathologies and that this amount varies inter alia, depending on the kind of hydroxyl radical scavenger used, the mode of administration, the severity of the condition to be treated, and the concentration of the compound in the therapeutic formulation. Generally, an amount of hydroxyl radical scavenger to be administered as a therapeutic agent for treating ROS induced pathologies such as atherosclerosis, cardiovascular disease, cancer, diabetes complications, muscular degeneration and arthritis; in particular atherosclerosis and cardiovascular disorders; will be determined on a case by case by an attending physician.

Generally, a suitable dose is one that results in a concentration of the hydroxyl radical scavenger at-the treatment site in the range of 100 nM to 100 uM, and more usually 500 nM to 10 uM To obtain these treatment concentrations, a patient in need of treatment likely will be administered an amount of about 1 mg to 5.0 g; in particular from about 10 to 1000 mg; in a further embodiment from 100 to 2500 mg; in an even further embodiment from 1 to 200 mg. As noted above, the above amounts may vary on a case-by-case basis. In these methods of treatment the compounds according to the invention are preferably formulated prior to admission. As described herein below, suitable pharmaceutical formulations are prepared by known procedures using well-known and readily available ingredients.

Without being limited to the below mentioned compounds and ranges, an exemplary table of hydroxyl radical scavengers with their range of suitable doses to be administered to warm-blooded animals, for example human beings, of, for example, approximately 70 kg body weight, is provided hereinafter.

Hydroxyl Radical Scavengers

Purified Natural Compounds or their Synthetic Counterpart

| Polyphenolic compounds | |
|---|---|
| Quercetin | 10-1000 mg |
| Genistein | 10-2500 mg |
| Resveratrol | 10-2500 mg |
| Oleuropein | 1-500 mg |
| Pycnogenol | 1-500 mg |
| Procyanidin C1 | 1-500 mg |
| Daidzein | 1-200 mg |
| Other organic compounds | |
| Thymoquinone | 1-50 micromoles |
| amino acids and derivatives | |
| N-acethyl cysteine | 10-3000 mg |
| Citrullin | 1-100 g |
| 5-Hydroxytryptophan (5-HTP) | 1-500 mg |

A particular group of hydroxyl radical scavengers as used in the examples hereinafter, consists of:

| | |
|---|---|
| Quercetin | 10-1000 mg |
| Resveratrol | 10-2500 mg |
| N-acethyl cysteine | 10-3000 mg |

Daily hydroxyl radical scavenger dosages required in practicing the method of the present invention will vary depending upon, for example the kind of hydroxyl radical scavenger used, the mode of administration and the severity of the condition to be treated. An indicated daily dose is in the range of from about 1 to about 5000 mg, e.g. from 10 to 1000 mg or from 100 to 2500 mg, or e.g. from 1 to 200 mg of active agent for oral use, conveniently administered once or in divided dosages. Single doses comprise, for example, 10, 50, 100, 200, 250, 300, 400, 500 or 1000 mg of active ingredient.

For the zinc, the second component of the combinations, kits of parts and pharmaceutical compositions of the present invention, the doses to be administered to warm-blooded animals, for example human beings, of, for example, approximately 70 kg body weight, are typically from 1 mg to approximately 1 g, for example from approximately 1 mg to approximately 100 mg, or for approximately from 25 mg to 750 mg, per person per day, in particular from about 10 to 500 mg, per person per day. Doses can be divided preferably into 1 to 4 single doses that may, for example, be of the same size. Usually, children receive about half of the adult dose. The dose necessary for each individual can be monitored, for example by measuring the serum concentration of the active ingredient, and adjusted to an optimum level. Single doses comprise, for example, 1, 5, 10, 20, 40, 50 or 100 mg of zinc.

In a particular embodiment the hydroxyl radical scavenger is Quercetin, which daily dosage is typically between 1 to about 5000 mg, e.g. from 10 to 1000 mg or from 100 to 2500 mg, or e.g. from 1 to 200 mg. Preferred examples of daily oral dosage are 50, 100, 200, 500, or 1000 mg. The application of the active ingredient may occur up to four times a day, preferably one or two times a day.

Corresponding doses may be taken, for example, in the morning, at mid-day or in the evening and as long as required (days, weeks, months or years) to see an improvement in oxidative stress parameters mentioned hereinbefore. Alternatively, and in particular when using the aforementioned components; combinations; in the prevention of ROS induced pathologies in women using oral contraceptives or on HRT, the corresponding doses can for example be used concurrent with and as long as oral contraceptives or HRT are used.

Given the particular application of the aforementioned components; combinations; in the prevention or treatment of oxidative stress induced pathologies in women using oral contraceptives or on HRT, as another aspect the present invention provides a combination of the aforementioned components; combinations; with another agent used in oral contraceptive or HRT.

Examples of other agents used in oral contraceptive include.

The Combined Oral Contraceptive Pill (COCP), often referred to as the birth-control pill, or simply "the Pill", is a combination of an estrogen (oestrogen) and a progestin (progestogen);

Progestogen Only Pills or Progestin Only Pills (POP) are contraceptive pills that only contain synthetic progestogens (progestins) and do not contain estrogen. Some examples of progestins that are used in hormonal contraceptives are mestranol; ethinyl estradiol and ethynodiol (Demulen); norethynodrel (Enovid); norethindrone (many brand names, most notably Ortho-Novum and Ovcon); norgestimate (Ortho Tricyclen, Ortho-Cyclen); norgestrel; levonorgestrel (Alesse, Trivora-28, Plan B); medroxyprogesterone (Provera, Depo-Provera); desogestrel (Ovidol); and drospirenone (Yasmin, Yasminelle, YAZ).

Ormeloxifene (also known as Centchroman) is one of the selective estrogen receptor modulators, or SERMs, a class of medication which acts on the estrogen receptor. It is best known as a non-hormonal, non-steroidal oral contraceptive which is taken once per week.

Examples of other agents used in HRT include.

For oral application, the hormones involved are typically selected from the group consisting of Estrogen, medroxyprogesterone, norgestimate, norethindrone, ethinyl estradiol, progesterone, norgestrel, progestin, 17β-estradiol, estrone, equilin, equilenin, estrone sulfate, and Phytoestrogens;

For injection (intra-muscular) the hormones are typically selected from estradiol cypionate and estradiol valerate;

For topical application the hormones are typically selected from Estrogen, and 17β-estradiol;

For transdermal application the hormones are typically selected from estradiol, and estradiol hémihydrate;

For vaginal application the hormone used in HRT typically consists of estradiol.

In a further aspect, the invention concerns a "kit-of-parts", combination, composition, use or a method as described herein, comprising or wherein the daily dosage administration is; i) between 10 and 5000 mg or between 50 and 1000 mg of an hydroxyl radical scavenger, in particular between 250 and 750 mg of a polyphenolic hydroxyl radical scavenger (such as quercetin), more in particular about 500 mg of quercetin, and ii) between 1 and 1000 mg or between 10 and 500 mg of zinc, in particular between 50 and 250 mg of zinc, more in particular about 100 mg of zinc or in any case, a pharmaceutically acceptable salt thereof.

In a further embodiment, the invention concerns a "kit-of-parts", combination, composition, use or a method as described herein, wherein the hydroxyl radical scavenger is selected from Quercetin, Genistein, Resveratrol, Oleuropein, Pycnogenol, Procyanidin, Daidzein, Thymoquinone, N-acethyl cysteine, Citrullin, 5-Hydroxytryptophan, in particular Quercetin, Genistein, Resveratrol; more in particular Quercetin.

Thus in an even further embodiment of the described "kit-of-parts", combinations, compositions, uses or methods of treatment, the hydroxyl radical scavenger is quercetin and the zinc is zinc gluconate or zinc acetate.

The structure of the active agents identified by generic or trade names (supra) may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The pharmaceutical compositions of the present invention can be prepared by any known or otherwise effective method for formulating or manufacturing the selected product form. Methods for preparing the pharmaceutical compositions according to the present invention can be found in "Remington's Pharmaceutical Sciences", Mid. Publishing Co., Easton, Pa., USA.

For example, the compounds can be formulated along with common excipients, diluents, or carriers, and formed into oral tablets, capsules, sprays, mouth washes, lozenges, treated substrates (e.g., oral or topical swabs, pads, or disposable, non-digestible substrate treated with the compositions of the present invention); oral liquids (e.g., suspensions, solutions, emulsions), powders, or any other suitable dosage form.

Non-limiting examples of suitable excipients, diluents, and carriers can be found in "Handbook of Pharmaceutical Excipients", Second edition, American Pharmaceutical Association, 1994 and include: fillers and extenders such as starch, sugars, mannitol, and silicic derivatives; binding agents such as carboxymethyl cellulose and other cellulose derivatives, alginates, gelatin, and polyvinyl pyrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as acetyl alcohol, glycerol monostearate; adsorptive carriers such as kaolin and bentonite; carriers such as propylene glycol and ethyl alcohol, and lubricants such as talc, calcium and magnesium stearate, and solid polyethyl glycols.

The invention furthermore relates to a commercial package comprising the combination according to the present invention together with instructions for simultaneous, separate or sequential use.

In one embodiment, the (commercial) product is a commercial package comprising as active ingredients the combination according to the present invention (in the form of two or three or more separate units of the components (a) or (b) as defined herein), together with instructions for its simultaneous, separate or sequential use, or any combination thereof, in the delay of progression or treatment of the diseases as mentioned herein. In a further embodiment, the package comprises one or more separate units containing the combination of the components (a) and (b), optionally containing further agents used in oral contraception or HRT. In an even further embodiment the package comprises one or more separate units of the components (a) or (b), wherein either the units containing component (a) or the units containing component (b), further comprise one ore more further agents used in oral contraception or HRT. In a particular embodiment, the units containing component (b) further comprise one ore more further agents used in oral contraception or HRT.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLES

The following examples illustrate the invention. Other embodiments will occur to the person skilled in the art in light of these examples.

1. Example 1

1.A Effect of Oral Contraception on the Oxidative Stress

First Study

Objectives

Evaluation of the influence of oral contraception with estrogens and progestins on several markers of the oxidative stress.

Material And Methods

A group of 78 women taking oral contraceptives (OC) containing estrogens and progestins has been compared to a matched control group of women without OC. The oxidative status included oligo-elements like copper and zinc and oxidative stress markers like lipid peroxides and oxidized LDL. Median values of the two groups were compared using appropriate statistical methods.

Results

Demographic and Anthropometric Data

Both groups did not differ significantly regarding age, body mass index (BMI) and addiction to smoking.

Biochemical Data

Figure 2:
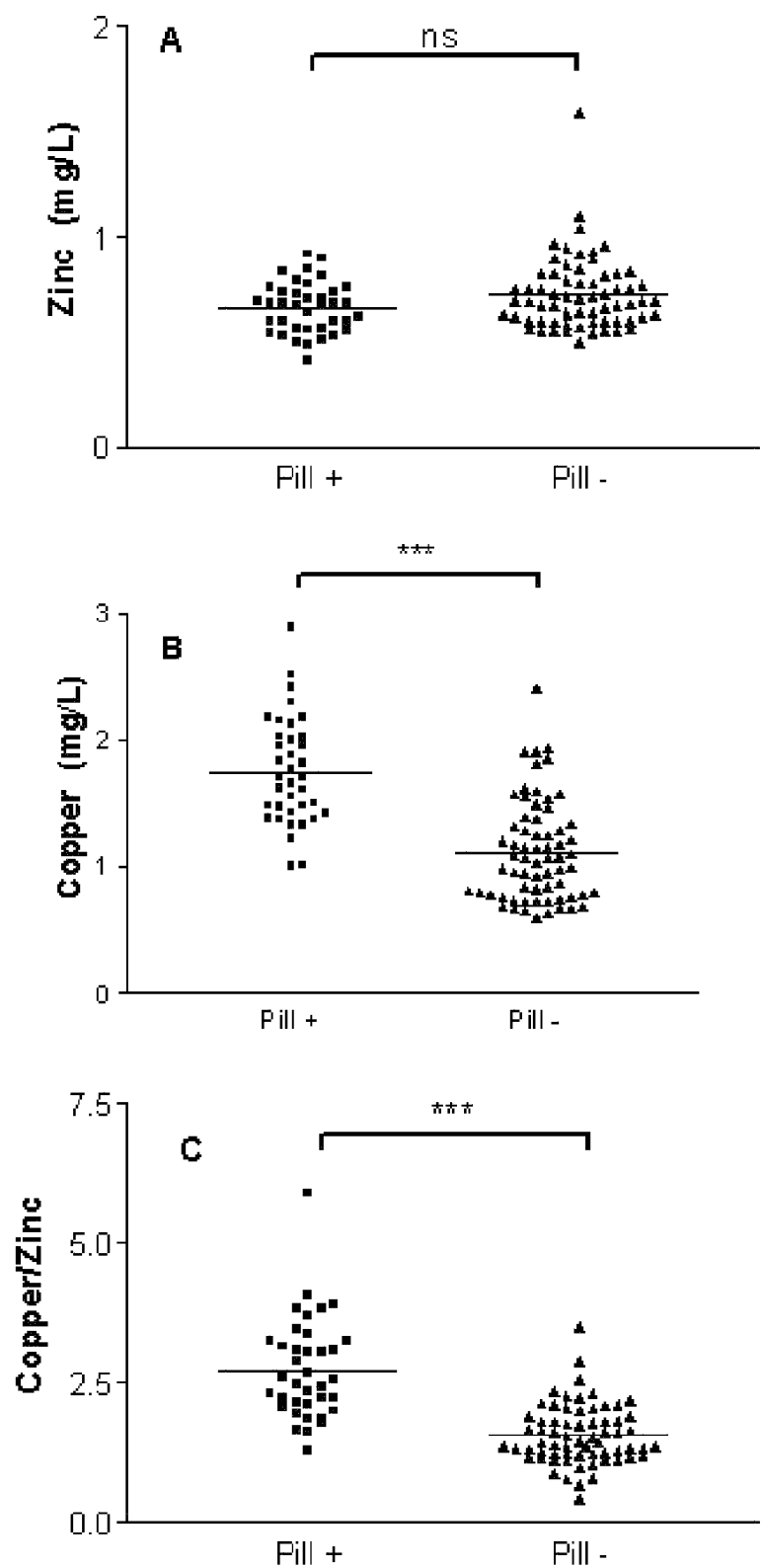
FIG. 2: Levels of zinc (panel A), copper (panel B), and Cu/Zn ratio (panel C) in women with ■ or without ▲ OC. Horizontal bars represent median values. Statistical differences: ***=Mann Whitney p 21 0.0001.
Figure 3:
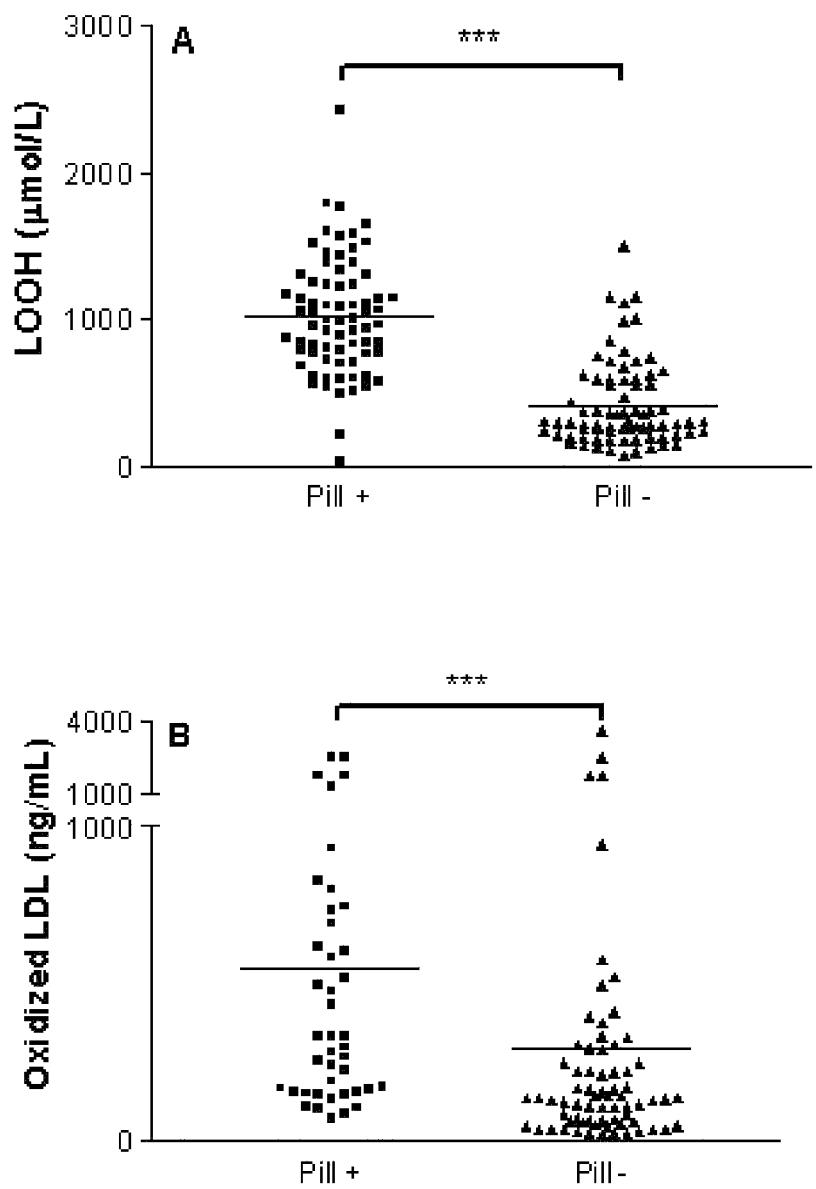
FIG. 3: Levels of lipid peroxides (panel A) and oxidized LDLs (panel B) in women with ■ or without ▲ OC. Horizontal bars represent median values. Statistical differences: *=Mann Whitney p<0.05 et ***=Mann Whitney p<0.0001.

Zinc levels were slightly lower in the OC group with regard to the group not taking the pill ($0.67\pm0.12$ mg $L^{-1}$ against $0.73\pm0.17$ mg $L^{-1}$, not statistically significant) (FIG. 2 panel A). The levels of copper and the copper/zinc ratio were very significantly higher in the OC group with regard to the group not taking the pill ($1.75\pm0.42$ versus $1.12\pm0.40$ mg $L^{-1}$, Mann Whitney $p<0.0001$ for copper and $2.74\pm0.90$ versus $1.57\pm0.53$ Cu/Zn, Mann Whitney $p<0.0001$ for the Cu/Zn ratio) (FIG. 2 panel B and C). Lipid peroxides and oxidized LDLs were also very significantly higher in the OC group with regard to the group not taking the pill ($1022\pm399$ µmol/L versus $418\pm292$ µmol/L, Mann Whitney $p<0.0001$ for lipid peroxides, $559\pm600$ versus $300\pm579$ ng $mL^{-1}$, Mann Whitney $p<0.0001$ for oxidized LDLs) (FIG. 3).

1.B Effect of Oral Contraception on the Oxidative Stress

Second Study

Objectives

Evaluation of the influence of oral contraception with estrogens and progestins on several markers of the oxidative stress.

Material And Methods

Sixty-two healthy female subjects participated in the study. The study was approved by and performed under the guidelines of the Ethic Committee of the University Hospital of Liege, Belgium and informed consent was obtained from each of the subjects before blood sampling. The test group consisted in 32 women who were regular OC users (OCU) since at least 2 months and who were recruited during routine gynecology visits. All the OCU were taking a contraceptive pill containing 0.03 mg ethinylestradiol and 3 mg drospirenon (DRSP). The control group consisted in 30 non-contraceptive users (NCU) with no other hormonal treatments who were recruited during routine gynecology or medically assisted reproduction visits.

All the subjects were of normal body weight and were nonsmokers with no evidence of chronic disease. None of the subjects consumed >25 mL alcohol/d or were taking other medications, antioxidants, or vitamin supplements. The mean (±SD) ages and body mass indexes (BMI) were, respectively, $29.4\pm4.3$ years and $23.7\pm2.8$ kg/m² for the NCU group and $23.0\pm3.9$ years and $21.3\pm2.9$ kg/m² for the OCU group.

Blood samples for the assessment of OS markers were taken between the third and fifth day of the menstrual cycle Median values of the two groups were compared using appropriate statistical methods.

Results

Levels of Zn ($0.73\pm0.15$ versus $0.75\pm0.10$ mg/L), Vit-E ($11.26\pm1.76$ versus $11.46\pm2.47$ mg/L) and antibodies to oxidized LDL (Ab-ox-LDL) ($555.0\pm501.4$ versus $530.5\pm447.5$ U/L) were not significantly different between the two groups. Significant increases in the mean levels of LOOH ($478.2\pm194.7$ versus $1321.9\pm356.9$ µmol/L, $p<0.001$), ox-LDL ($503.9\pm536.3$ versus $1236.3\pm1023.8$ ng/mL, $p<0.002$), Cu ($0.86\pm0.23$ versus $1.75\pm0.36$ mg/L, $p<0.001$), Cu/Zn ratio ($1.18\pm0.21$ versus $2.37\pm0.39$, $p<0.001$) and a significant decrease in the mean level of (β-carotene ($0.35\pm0.22$ versus $0.20\pm0.07$ mg/L, $p<0.01$) were observed in the OCU compared to NCU (Table 1).

TABLE 1

Biochemical values in non-contraceptive users (NCU) and oral contraceptive users (OCU).

| | NCU (n = 30) | OCU (n = 32) | p value between groups |
|---|---|---|---|
| Lipid peroxides (mmol/L) | 478.2 (194.7) | 1321.9 (356.9) | <0.001 |
| Oxidized LDL (ng/mL) | 503.9 (536.3) | 1236.3 (1023.8) | 0.0015 |
| Ab-ox-LDL (U/mL) | 555.0 (501.4) | 530.5 (447.5) | ns |
| α-tocopherol (mg/L) | 11.26 (1.76) | 11.46 (2.47) | ns |
| β-carotene (mg/L) | 0.35 (0.22) | 0.20 (0.07) | 0.0086 |
| Copper (mg/L) | 0.86 (0.23) | 1.75 (0.36) | <0.001 |
| Zinc (mg/L) | 0.73 (0.15) | 0.75 (0.10) | ns |
| Cu/Zn ratio | 1.18 (0.21) | 2.37 (0.39) | <0.001 |

Values are means (S.D.). Differences between groups are statistically significant for $p<0.05$.

Discussion

Figure 4:
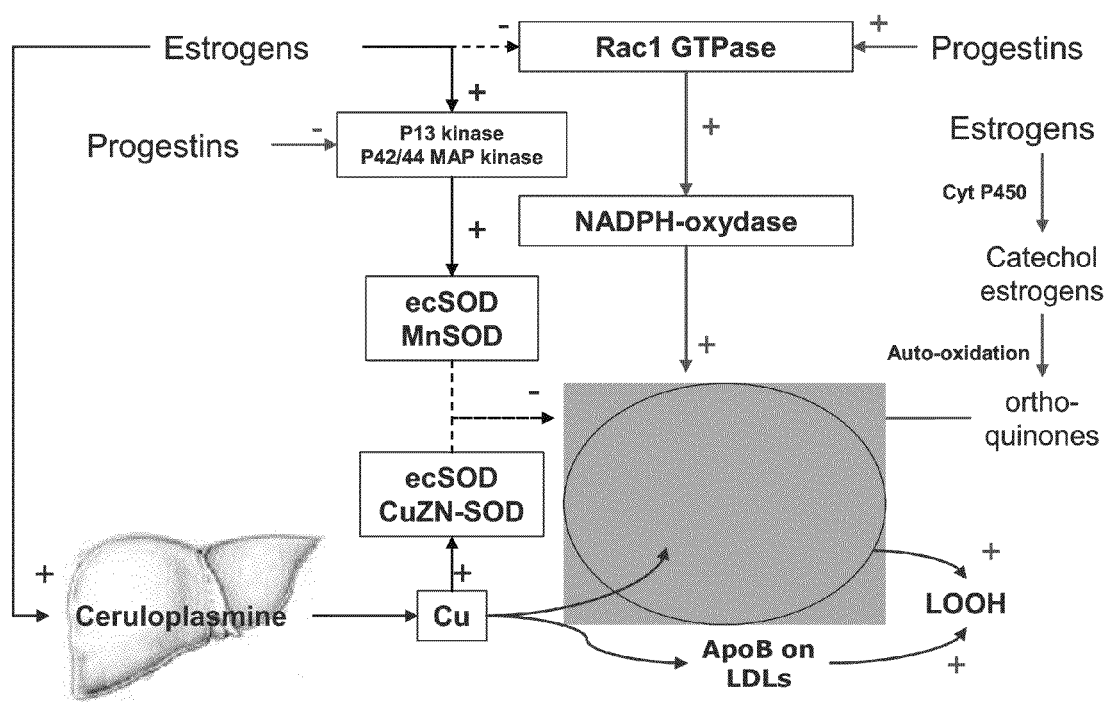
FIG. 4: Schematic representation of estrogens and progestins metabolic pathways involved in oxidative stress and lipid peroxidation.

The plasma increase of the lipid peroxides associated to estrogen+progestin contraceptives that we observed can be explained by opposite effects of estrogens and progestin on the metabolic pathways and on the mechanisms of regulation of the oxidative stress (see FIG. 4). Indeed, estrogens display an antioxidant activity by inhibiting the expression and function of the NADP+/NADPH oxidase (Wagner A H, Schroeter M R, Hecker M. 17beta-estradiol inhibition of NADPH oxidase expression in human endothelial cells. FASEB J. 2001 October; 15 (12):2121-30) (Laufs U, Adam O, Strehlow K, Wassmann S, Konkol C, Laufs K et al. Down-regulation of Rac-1 GTPase by Estrogen. J Biol Chem. 2003 Feb. 21; 278 (8):5956-62. Epub 2002 Dec. 18), by increasing the expression and level of activation of the endothelial isoform of the nitric oxide synthetase (eNOS) (Chambliss K L, Shaul P W. Estrogen modulation of endothelial nitric oxide synthase. Endocr Rev. 2002 October; 23 (5):665-86) and by stimulating the expression and the activity of the manganese SOD (MnSOD) and of the extracellular SOD (ecSOD) (Strehlow K, Rotter S, Wassmann S, Adam O, Grohe C, Laufs K et al. Modulation of antioxidant enzyme expression and function by estrogen. Circ Res. 2003 Jul. 25; 93 (2):170-7). These anti-oxidant activities of estrogens are counteracted by progestins via the activation of the NADPH oxidase and the inhibition of the expression and activity of the MnSOD and of the ecSOD (Wassmann K, Wassmann S, Nickenig G. Progesterone antagonizes the vasoprotective effect of estrogen on antioxidant enzyme expression and function. Circ Res. 2005 Nov. 11; 97 (10):1046-54)(Itagaki T, Shimizu I, Cheng X, Yuan Y, Oshio A, Tamaki K et al. Opposing effects of oestradiol and progesterone on intracellular pathways and activation processes in the oxidative stress induced activation of cultured rat hepatic stellate cells. Gut. 2005 December; 54 (12):1782-9).

A direct pro-oxidant effect of estrogens was shown in experimental models in the rat (Gordon K B, Macrae I M, Carswell H V. Effects of 17beta-oestradiol on cerebral ischaemic damage and lipid peroxidation. Brain Res. 2005 Mar. 2; 1036 (1-2):155-62) and the Syrian hamster (Bhat H K, Calaf G, Hei T K, Loya T, Vadgama J V. Critical role of oxidative stress in estrogen-induced carcinogenesis. Proc Natl Acad Sci USA. 2003 Apr. 1; 100 (7):3913-8). These pro-oxidant effects of estrogens can partially be explained by their metabolism. Indeed, estrogens can be metabolically activated into catechol estrogens by the enzymes of the cytochrome P450. These last ones are easily auto-oxidized in ortho-quinone by-products which are powerful oxido-reducing agents capable of generating ROS (Prokai-Tatrai K, Prokai L. Impact of metabolism on the safety of estrogen therapy. Ann NY Acad Sci. 2005 June; 1052:243-57).

The increase of serum copper related to the OCs use is known and has been attributed to the induction by estrogens of the hepatic release of ceruloplasmin, the main copper carrier protein (Akhter S, Shamsuzzaman A K, Banarjee M, Seema S A, Deb K. Serum copper in rural women taking combined oral contraceptive. Mymensingh Med J. 2006 January; 15 (1):25-9) (Berg G, Kohlmeier L, Brenner H. Effect of oral contraceptive progestins on serum copper concentration. Eur J Clin Nutr. 1998 October; 52 (10):711-5). The copper and the zinc are trace elements which play a vital role as catalytic co-factors for a variety of enzymes including CuZn—SOD, an enzyme which participates actively in the elimination of ROS (Uriu-Adams J Y, Keen C L. Copper, oxidative stress, and human health. Mol Aspects Med. 2005 August-October; 26 (4-5):268-98). An unbalance between these two trace elements could result in a dysfunction of CuZn—SOD, and consequently, a decrease of the protection of lipids against oxidation by ROS. There are numerous evidences which suggest that the copper plays a direct role in the lipid peroxidation (Ferns G A, Lamb D J, Taylor A. The possible role of copper ions in atherogenesis: the Blue Janus. Atherosclerosis. 1997 September; 133 (2):139-52. Review.) (Ferns G A, Lamb D J, Taylor A. The possible role of copper ions in atherogenesis: the Blue Janus. Atherosclerosis. 1997 September; 133 (2):139-52. Review) (Patel R P, Svistunenko D, Wilson M T, Darley-Usmar V M. Reduction of Cu(II) by lipid hydroperoxides: implications for the copper-dependent oxidation of low-density lipoprotein. Biochem J. 1997 Mar. 1; 322 (Pt 2):425-33). The copper is a pro-oxidant redox-active transition metal while zinc, which is redox-inactive, is capable of counteracting the pro-oxidant activity of copper (Bray T M, Bettger W J. The physiological role of zinc as an antioxidant. Free Radic Biol Med. 1990; 8 (3):281-91).

Conclusions

In view of these results, we suggest the use of a combination of zinc and of a hydroxyl radical scavenger to block the OC-induced oxidative stress process at different levels (FIG. 1). Zinc will be used to inhibit copper intake, antagonize copper catalyze of hydroxyl production from superoxide and $H_2O_2$ and remove copper from binding site where it cause radicals formation (Prasad A S, Bao B, Beck F W, Kucuk O, Sarkar F H. Antioxidant effect of zinc in humans. Free Radic Biol Med. 2004 Oct. 15; 37 (8):1182-90) (Gaetke L M, Chow C K. Copper toxicity, oxidative stress, and antioxidant nutrients. Toxicology. 2003 Jul. 15; 189 (1-2):147-63) (Powell S R. The antioxidant properties of zinc. J Nutr. 2000 May; 130 (5S Suppl):1447S-54S.). Remaining hydroxyl radicals will then be eliminated by a specific scavenger.

2. Example 2

Clinical Study to Assess the Effect of Zinc and Hydroxyl Radical Scavenger on OC-Induced Oxidative Stress in Women The purpose of this study was to objectivize the potential effect of zinc and quercetin intake, at doses that are considered as nutritional supplements, on blood (biochemical and biomolecular) parameters linked to the oxidative stress, inflammation and atherosclerosis, induced by an estroprogestative-based contraceptive treatment. This study was conducted from January 2009 to June 2010 in Liège, Belgium.

A. Study Design

Four Arms Single Blind Placebo Controlled Study

Subjects: 60 women were selected on the basis of the below-mentioned selection criteria and divided into 4 groups. Keeping a possible dropout in mind (in total 45 women completed the study), these groups were designed such, that by the end of the study; groups SOCO_A and SOCO_D would contain 15 subjects; and groups SOCO_B and SOCO_C would contain 10 subjects.

Figure 10:
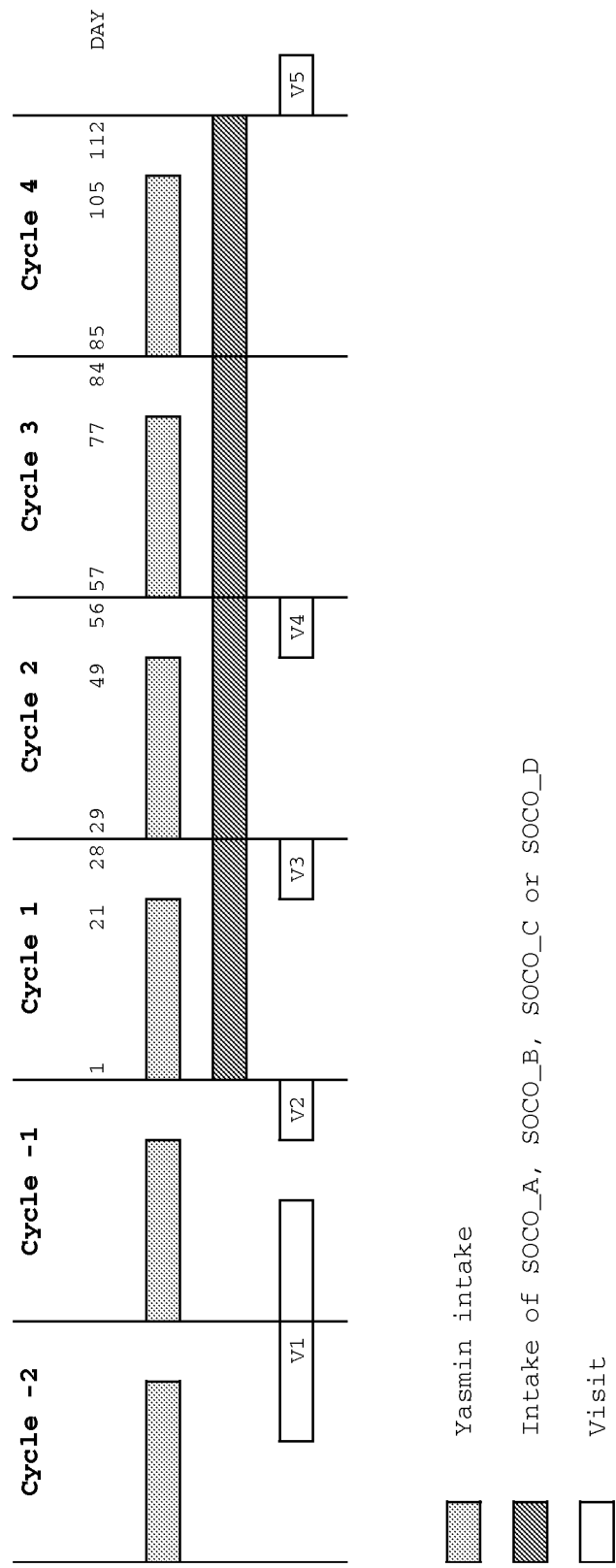
FIG. 10: Scheme of menstrual cycles with regard to Vitamin intake and oral contraceptive treatment.

Inclusion Criteria:
Age: between 18 and 35 years
Informed consent collected
Patients under oral contraception with Yasmin for at least three months
Exclusion Criteria:
Type I and II diabetes
Participation in other clinical studies, which have ended until less than 6 months ago
High blood pressure (PA≥140/90 mmHg)
Low blood pressure (PA≤100/×mmHg)
Disturbances of the coagulation
Morbid obesity (BMI≥30)
Anorexia (BMI≤17.5)
Tobacco addiction
General contraindications to an oral contraception
Pregnancy
Endocrino-dependent tumours Thyroid anomalies Chronic or acute vascular, renal or hepatic pathologies Vitamins C, E, trace elements such as zinc, copper and iron, antioxidants or vitamin complexes intake The study was conducted during 6 consecutive menstrual cycles as shown in FIG. 10.

Whereby one menstrual cycle is flanked by 2 vertical lines and, whereby:
- SOCO_A) represents the intake of a combination of a Zinc supplement and a Quercetin supplement
- SOCO_B) represents the intake of a Zinc supplement
- SOCO_C) represents the intake of a Quercetin supplement
- SOCO_D) represents the intake of a placebo supplement And whereby:
- V1 represents a first visit between day −42 and day −14
- V2 represents a second visit between day −7 and −3
- V3 represents a third visit between day 23 and 27
- V4 represents a fourth visit between day 51 and 55
- V5 represents a fifth visit between day 113 and 117

Composition and Method of Intake of the Formulations:

Yasmin: Drospirenone 3 mg

Ethinylestradiol 30 µg 1 tablet per day at the same time of the day during 21 consecutive days followed by 7 days without treatment SOCO_A: Quercetin DC 500 mg Zinc picolinate 20% (elementary 22.5 mg) 113 mg Magnesium stearate 3 mg 1 capsule per day during 112 days SOCO_B: Zinc picolinate 20% (elementary 22.5 mg) 113 mg Dicalcium phosphate 125 mg Cellulose microcrystals 375 mg Magnesium stearate 3 mg 1 capsule per day during 112 days SOCO_C: Quercetin DC 500 mg Dicalcium phosphate 85 mg Cellulose microcrystals 28 mg Magnesium stearate 3 mg 1 capsule per day during 112 days SOCO_D: Dicalcium phosphate 460 mg Cellulose microcrystals 153 mg Magnesium stearate 3 mg 1 capsule per day during 112 days Subjects were not informed about the nature of the capsules administered in supplement of the oral contraceptive (Yasmin). They received one pot containing 28 capsules of their corresponding group at V2 and V3 and 2 pots containing 28 capsules of their corresponding group at V4.

B. Parameter Assessment

A blood sample (2-3 tubes of +/−5 ml) was collected during each visit. A maximum of 60 ml blood was required per subject for the whole study. Blood samples for haematological and biochemical tests were collected during V1 and V5, and blood samples for oxidative stress assessment were collected during V2, V3, V4 and V5.

Haematological and biochemical tests were performed after V1 and V5 in order to screen subjects according to the inclusion/exclusion criteria and to assess the tolerance to the study product. These analyses comprised:
- General physical status at the time of medical examination (weights, physical status such as cardiovascular, ENT, pulmonary, neurological, gastro-intestinal, dermatologic, endocrinologic and urogenital)
- Vital signs (heart rate, blood pressure)
- Laboratory exams
- Serious adverse events.

Plasma concentration of lipid peroxides, copper and zinc were determined in blood samples taken at V2, V3, V4 and V5. Plasma concentration of oxidized LDL was determined in blood samples taken at V2 and V5. The expression of 200 genes involved in oxidative stress were determined via quantitative measurements of mRNA expression by microarray, in blood samples taken at V2 and V5.

C. Effect Assessment

The main criterion of effect appraisal is a significant reduction of the lipidic peroxides, oxidized LDL or both parameters after combining intake of quercetin and zinc compared with intake of the placebo.

Secondary criteria of effect appraisal are:
1. A more significantly important reduction of the lipid peroxides, oxidized LDL or both parameters after the combined intake of quercetin and zinc compared with a possible reduction noticed after the intake of zinc or quercetin alone.
2. A significant modification of gene expression profile suggesting an improvement of the subjects oxidative stress status after the combined intake of quercetin and zinc compared with profiles noticed after the intake of zinc or quercetin alone.
3. An unexpected reduction of the lipid peroxides, oxidized LDL or both parameters after the intake of zinc or quercetin alone in comparison to what is usually described in scientific literature.

D. Tolerance Assessment

Following parameters were recorded to assess the tolerance to the study product:
- General physical status at the time of medical examination (weight, physical status such as cardiovascular, ENT, pulmonary, neurological, gastro-intestinal, dermatologic, endocrinologic and urogenital)
- Vital signs (heart rate, blood pressure)
- Laboratory tests
- Serious adverse events E. Compliance Assessment Compliance in the treatment was determined by an accounting of the capsules. Volunteers were asked to bring back all unused capsules as well as empty pots at every visit. Unused capsules were counted and recorded in the CRF. Compliance was considered as good if ≥80% of capsules had been taken, as middle if <70% to 80% of capsules had been taken and as poor if <70% of capsules had been taken.

F. Results of Biochemical Tests

Figure 5:
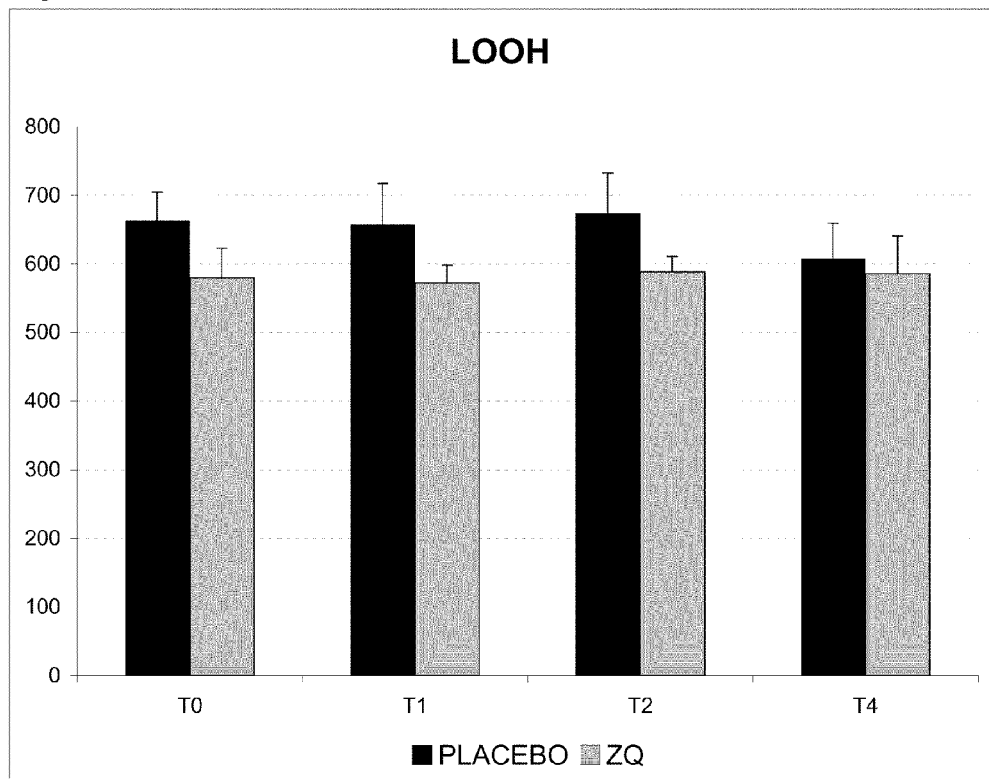
FIG. 5: Plasma concentration of A. lipid peroxides (LOOH), B. copper and C. Zinc as well as D. the ratio of Cu/Zn as determined in blood samples taken at T0, T1, T2 and T4 from individuals treated with Zinc and quercetin or with a placebo.
Figure 5:
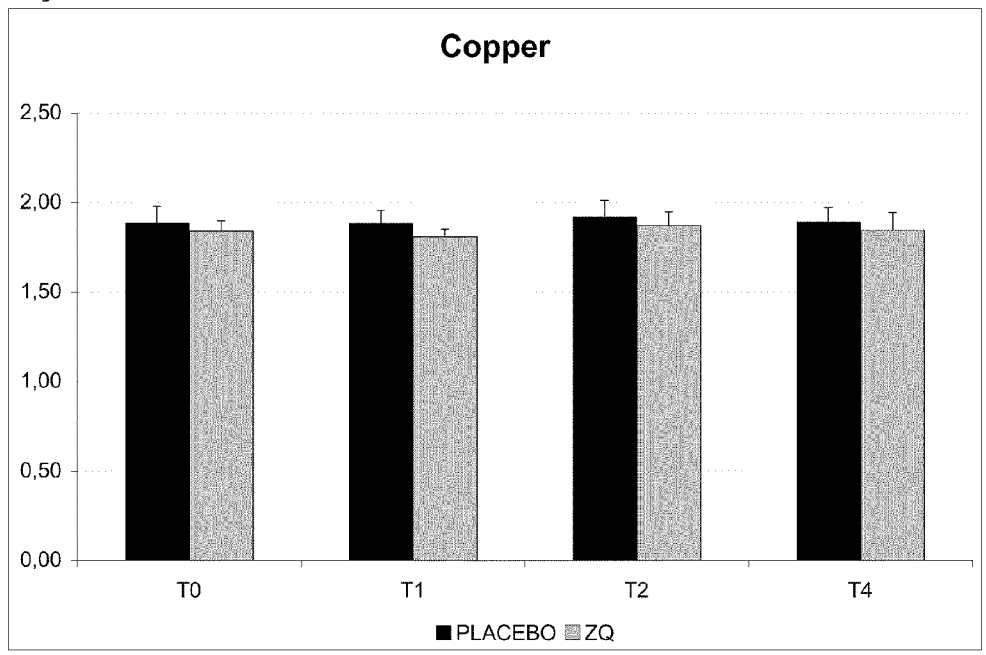
Figure 5:
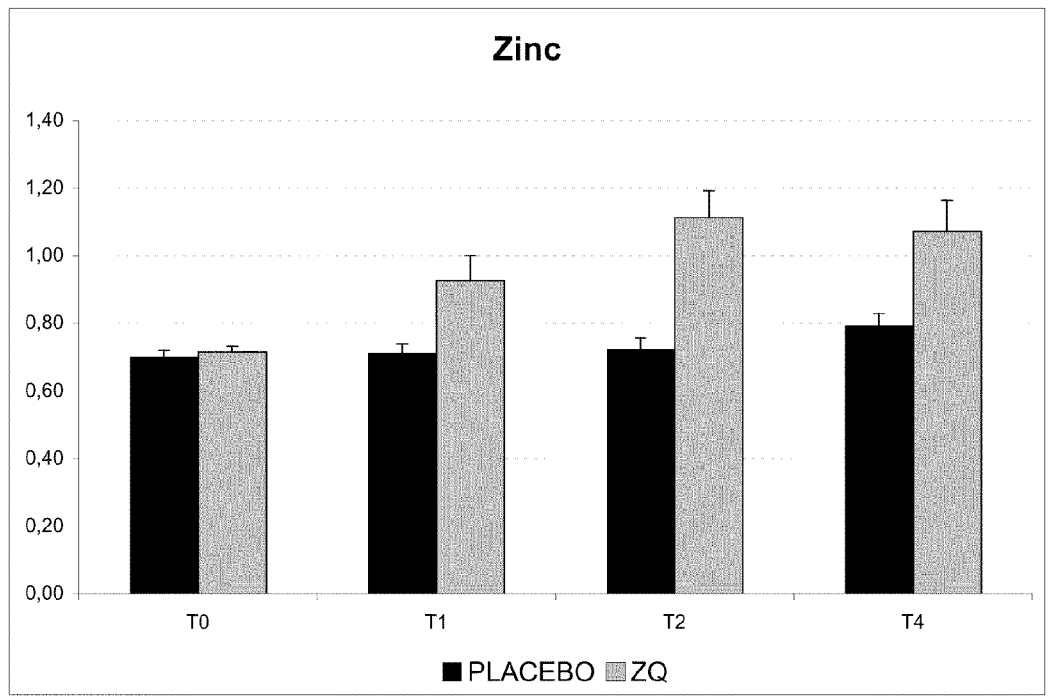
Figure 5D:
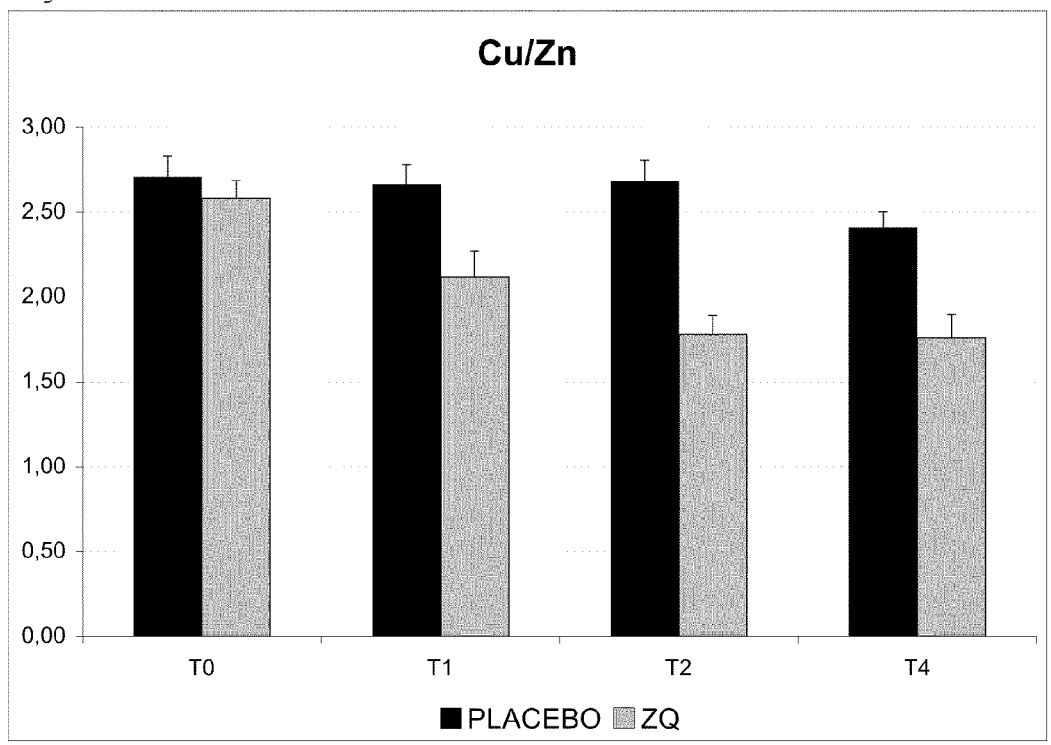

Plasma concentration of lipid peroxides (LOOH), copper and zinc, determined in blood samples taken at T0 (V2), T1 (V3), T2 (V4) and T4 (V5), are shown in FIG. 5. As evident, intake of the combination of Zinc and quercetin shows a significant increase in plasma Zinc concentrations and an improvement of the Cu/Zn ratio, compared to intake of placebo (Repeated paired measures ANOVA <0.0001).

Figure 6A:
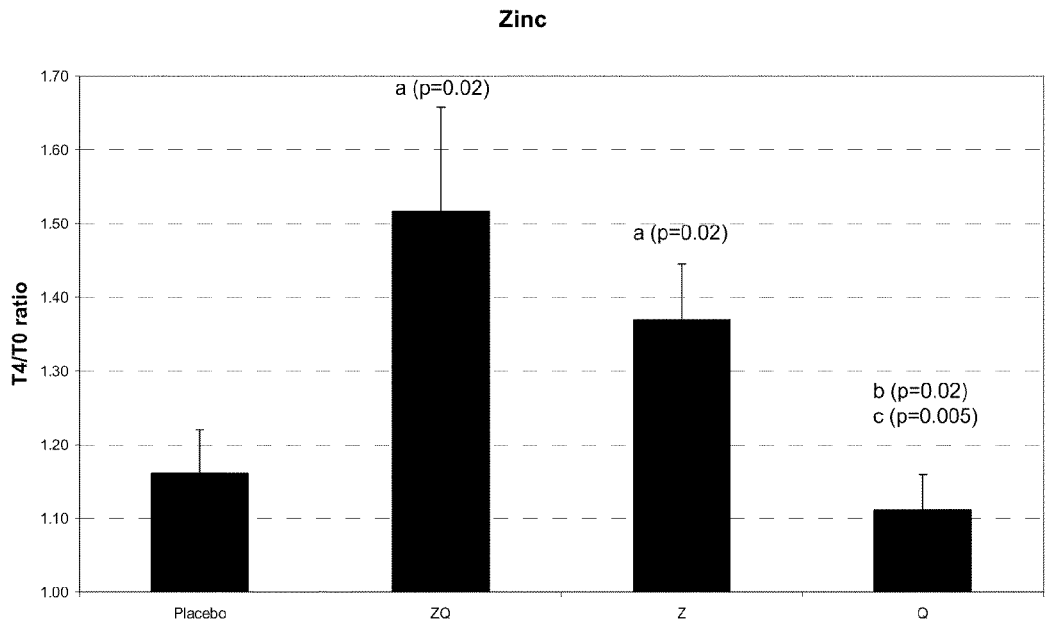
FIG. 6: Relative change of A. copper and B Cu/Zn ratio between T4 and T0 in the four arms. TTest p compared to placebo (a), zinc and quercetin (b) or zinc alone (c).

The mean relative change in Zn between T4 and T0 are represented in FIG. 6A. The mean zinc increase was significant between treatment with Zinc and quercetin and the placebo (p=0.02), between treatment with zinc alone and placebo (p=0.02), between the treatment with Zinc and quercétine and the treatment with quercetin alone and between the treatment with Zinc alone and quercetin alone (p=0.005).

Figure 6B:
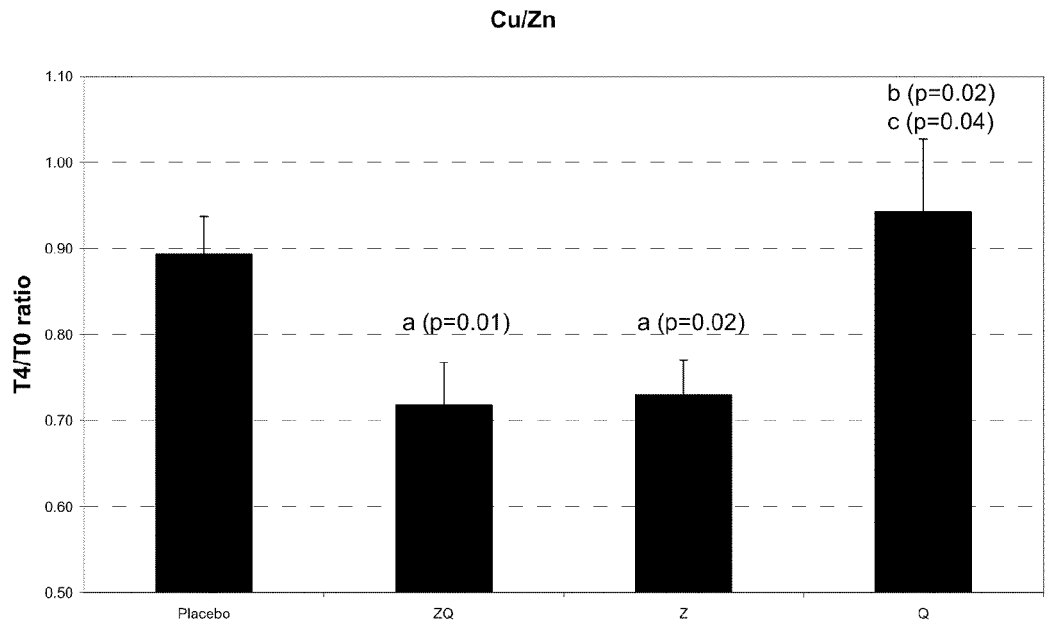
Figure 7A:
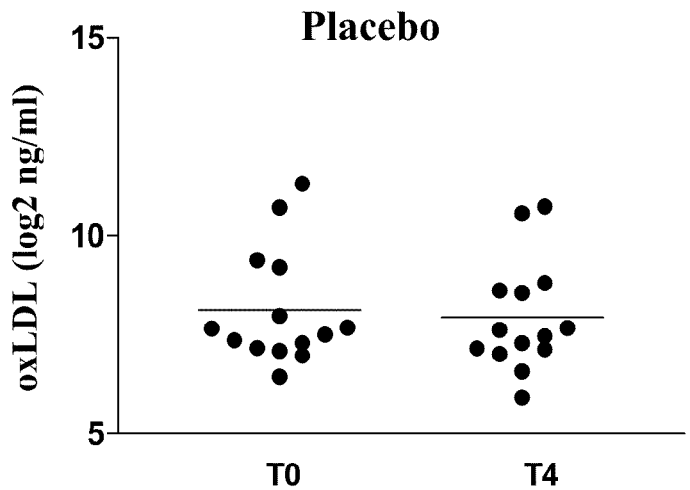
FIG. 7: Plasma concentration of oxidized LDL in blood samples taken at T0 and T4 from individuals treated with A. a placebo, B. Zinc and quercetin, C. Zinc alone or D. quercetin alone.
Figure 7B:
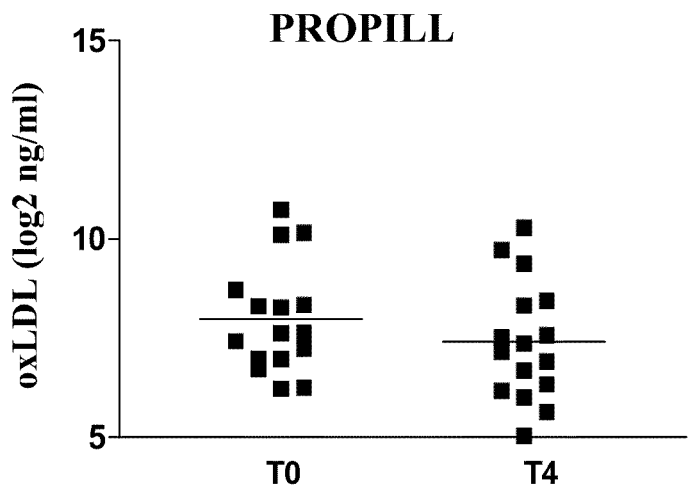
Figure 7C:
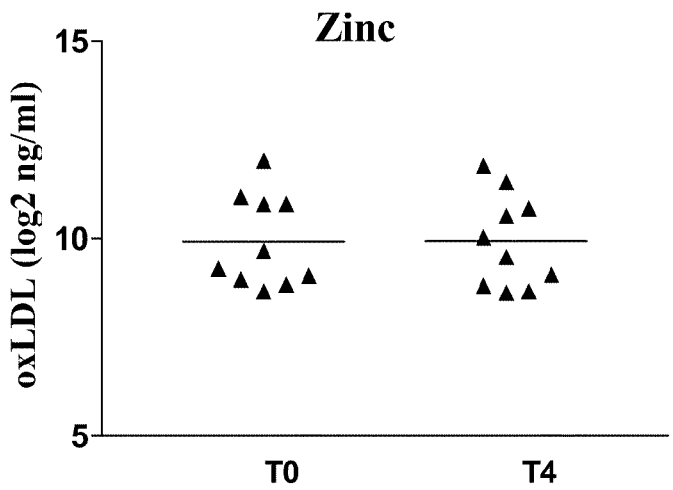
Figure 7D:
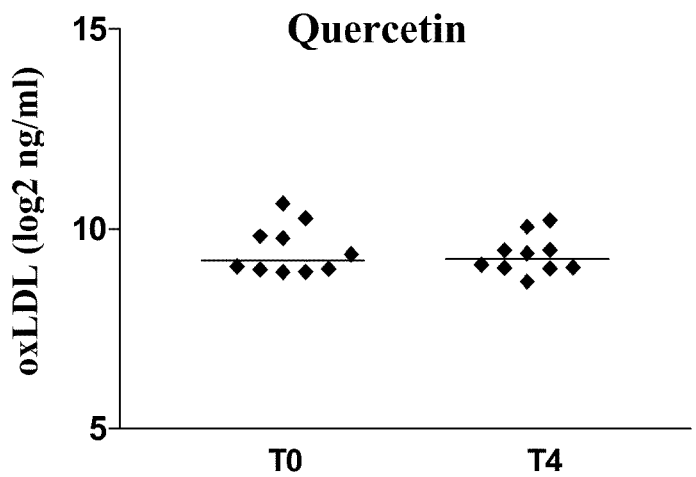

The mean relative change in Cu/Zn between T4 and T0 are represented in FIG. 6B. The mean Cu/Zn decrease was significant between treatment with Zinc and quercetin and the placebo (p=0.01), between treatment with zinc alone and placebo (p=0.02), between the treatment with Zinc and quercétine and the treatment with quercetin alone and between the treatment with Zinc alone and quercetin alone (p=0.04).

As already described earlier, an improvement of the balance between Zn (anti-oxidant) and Cu (pro-oxidant) is considered to protect LDLs from oxidaton (Uriu-Adams J Y et al., Mol Aspects Med. 2005 August-October; 26 (4-5):268-98; Ferns G A et al., Atherosclerosis. 1997 September; 133 (2):139-52; Patel R P et al., Biochem J. 1997 Mar. 1; 322 (Pt 2):425-33; Bray T M et al., Free Radic Biol Med. 1990; 8 (3):281-91; Mezzetti A et al., Free Radic Biol Med. 1998 October; 25 (6):676-81). No significant effect on lipid peroxides has been observed.

Figure 8:
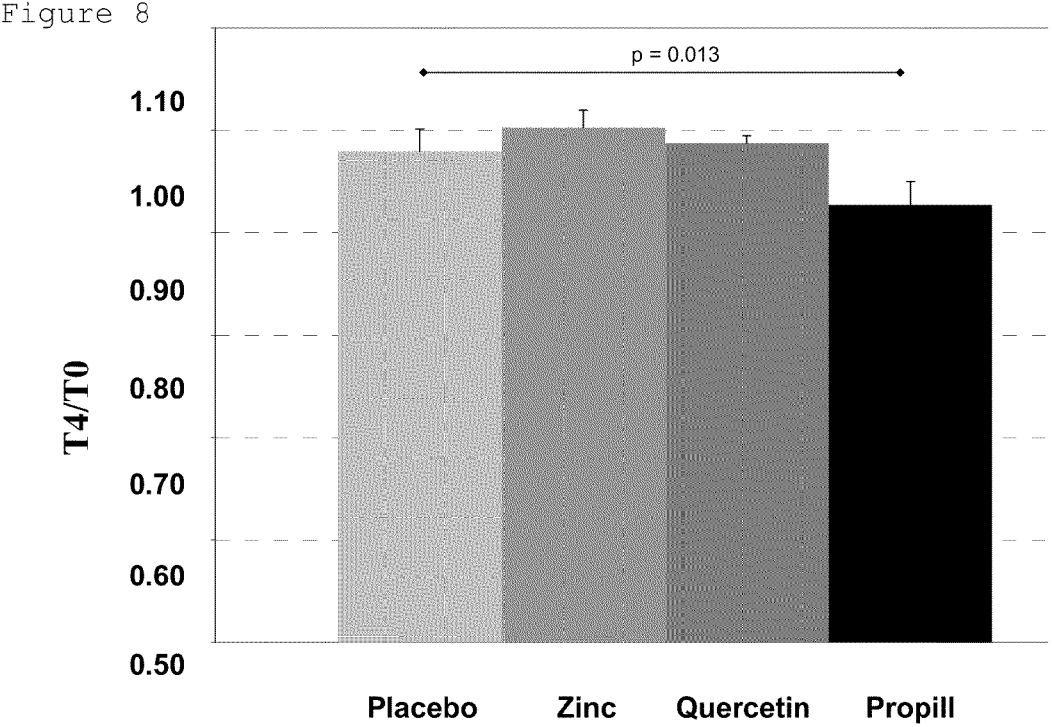
FIG. 8. Relative change (%) of oxLDL levels between T4 and T0 in the four arms.

Furthermore, the results of the analysis of oxLDL at T0 (V2) and T4 (V5) are represented in FIG. 7. The treatment with Zinc and quercetin shows a highly significant decrease (p=0.002) at T4 compared to T0 and the treatment with quercetin alone shows only a weak significant decrease (p=0.049), whereas no significant changes were observed for the placebo and the Zinc alone arms. The mean relative change in ox LDL between T4 and T0 are represented in FIG. 8. The mean difference (−5%) was significant between treatment with Zinc and quercetin and the placebo (p=0.013). In addition the number of responders (showing a minimum of 35% decrease of oxLDL) is significantly higher in the group treated with Zinc and Quercetin (50%) compared to the placebo group (14.3%, Chi Squared p=0.038), to the Zinc alone group (0%, Chi Squared p=0.007) and to the quercetin alone group (0%, Chi Squared p=0.007). The differences were not significant between the placebo and the Zinc alone group and between the placebo and the quercetin alone group/

As already described earlier, a reduction of atherogenic LDL oxidation has been shown to reduce the risk of vascular diseases, since oxLDL is involved in the formation of the atheromatous plaques (Hulthe J et al., Arterioscler Thromb Vasc Biol. 2002 Jul. 1; 22 (7):1162-7; Holvoet P et al., Acta Cardiol. 2004 October; 59 (5):479-84; Sigurdardottir V et al., Atherosclerosis. 2007 January; 190 (1):187-93; Girona J et al., Nutr Metab Cardiovasc Dis. 2008 June; 18 (5):380-7).

G. Results of Micro-Array Analysis

Figure 9:
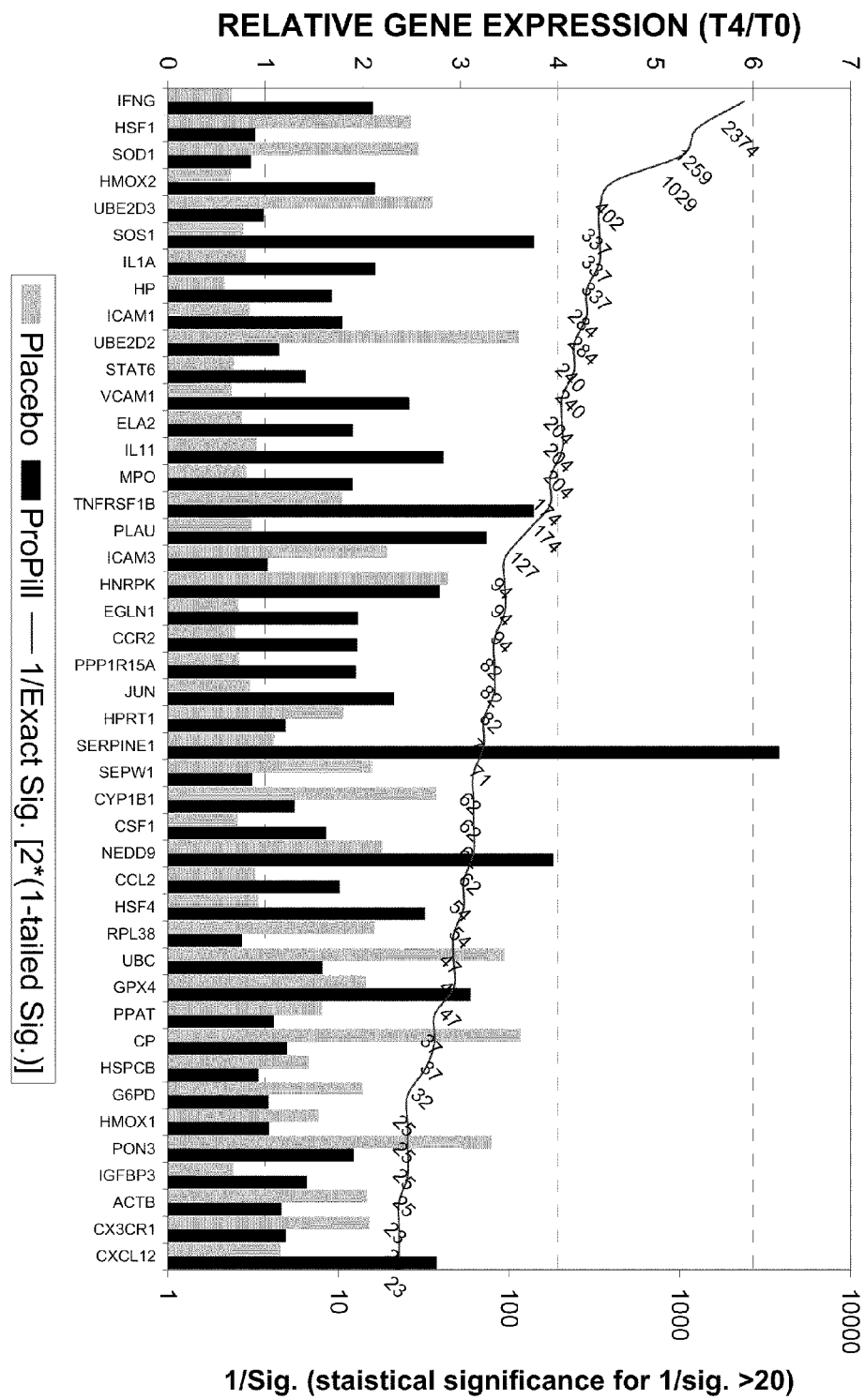
FIG. 9: Differential gene expression as determined via microarray in blood samples taken at T0 and T4 from individuals treated with Zinc and quercetin or with a placebo.

The expression of 200 genes involved in oxidative stress was determined via quantitative measurements of mRNA expression by microarray, in blood samples taken at T0 (V2) and T4 (V5). The analyses revealed 44 genes to be significantly differentially expressed in the group treated with Zinc and quercetin compared to the placebo group (p<0.05) (FIG. 9).

The observed gene profile suggests that the treatment with Zinc and quercetin regulates the expression of genes involved in different biological pathways (immunity, cell proliferation, response to stress, antioxidants . . . ).

For example, the expression of IFNγ, a marker of T1 immunity was significantly increased (p<0.0005) in the ZN/Q treated group compared to the placebo group. It has been shown in literature that TH1 immunity is impaired by progestins and can be activated by quercetin (Tait A S et al., J Leukoc Biol. 2008 October; 84 (4):924-31; Trunova N et al., Virology. 2006 Aug. 15; 352 (1):169-77. Epub 2006 May 30; Park H J et al., Int Immunopharmacol. 2009 March; 9 (3): 261-7; Nair M P et al., Biochim Biophys Acta. 2002 Dec. 16; 1593 (1):29-36).

As an other example, the expression of UBE2D3, an activator of NFκB translocation, is decreased. It has been shown in literature that E2 activates NFκB and that quercetin is able to decrease the expression of UBE2D3 and consequently the activity of NFκB (Stefani M et al., Ann NY Acad Sci. 2007 October; 1114:407-18; Cutolo M et al., Rheumatology (Oxford). 2008 June; 47 Suppl 3:iii2-5; Cutolo M et al., Arthritis Res Ther. 2005; 7 (5):R1124-32; Cutolo M et al., Lupus. 2004; 13 (9):635-8; Cutolo M et al., Clin Exp Rheumatol. 2003 November-December; 21 (6):687-90; Dai R et al., J Immunol. 2009 Dec. 1; 183 (11):6998-7005; Liu X J et al., Pharmazie. 2010 February; 65 (2):127-31).

In conclusion, the treatment with Zinc and quercetin can reverse the negative effect of progetins or estrogens on different biological pathways by modulating the expression of specific genes.

H. General Conclusion

This study clearly shows:
1. A very good biodisponibility of Zn present in the ProPill formulation
2. A significant improvement of the Cu/Zn ratio
3. A significant effect of the treatment with Zinc and quercetin on the reduction of LDL oxidation
4. Only a weak effect of the treatment with quercetin alone on LDL oxidation
5. No effect of the treatment with Zinc alone on LDL oxidation These effects can be attributed to a synergistic effect of Zinc and quercetin and are particularly favorable regarding the implication of oxLDL in the atherogenic process 6. The analysis of gene expression shows a significant modulation of 44 genes that are involved in different biological pathways (immunity, cell proliferation, response to stress, antioxidants . . . )

Most of these effects can be attributed to a direct or indirect effect of quercetin on gene expression. They are particularly favourable as they reverse some negative effects associated to oral contraception.

In conclusion, Zn and quercetin have synergistically and complementary effects that are beneficial for health in women under oral contraception with estradiol and progestines

The invention claimed is:

1. A combination comprising a) zinc, b) quercetin, and c) an active ingredient used in oral contraceptive treatment or hormone replacement therapy selected from the group consisting of estrogen, progestin, or a combination thereof.

2. The combination according to claim 1, wherein zinc is selected from the group consisting of mineral zinc complexes; zinc salts; zinc pyrithione; zinc acetate; zinc gluconate; zinc picolinate; zinc sulfate; zinc citrate; zinc glycerate; zinc monomethionine; zinc aspartate; zinc lactate, zinc malate; zinc tartrate; zinc orotate and zinc aminoacid chelates.

3. The combination according to claim 1, wherein said zinc component a), said quercetin component b), and said active ingredient c) are present in the same or separate compositions.

4. A kit of parts comprising a first component (a) which is zinc, a second component (b) which is quercetin, and an active ingredient (c) used in oral contraceptive treatment or hormone replacement therapy selected from the group consisting of estrogen, progestin, or a combination thereof.

5. A kit of parts as claimed in claim 4, wherein components (a), (b), and (c) are suitable for sequential, separate and/or simultaneous use in treating reactive oxygen species (ROS) induced pathologies in a subject in need thereof.

6. The combination according to claim 1, wherein the zinc is present in an amount of about 1 to 100 mg per dosing unit.

7. The combination according to claim 1, wherein quercetin is present in an amount of about 1 mg to 5 g per dosing unit.

8. The combination according to claim 1 wherein quercetin is present in an amount of about 10 to 1000 mg per dosing unit.

9. The combination according to claim 1 wherein quercetin is present in an amount of about 10 to 2500 mg per dosing unit.

10. The combination according to claim 1 further comprising diluents, excipients and/or inert carriers.

11. The combination according to claim 1, further comprising vitamins selected from the group consisting of alpha and beta carotene, biotin, vitamin A, vitamin B2, vitamin B6, vitamin B12, vitamin C, vitamin D, vitamin E and vitamin K.

12. The combination according to claim 1, further comprising minerals selected from the group consisting of chromium, manganese, molybdenum, magnesium, potassium and selenium.

* * * * *